US011020089B2

(12) United States Patent
Corl (10) Patent No.: US 11,020,089 B2
(45) Date of Patent: Jun. 1, 2021

(54) INTRAVASCULAR IMAGING DEVICES HAVING A LOW REVERBERATION HOUSING AND ASSOCIATED SYSTEMS AND METHODS

(71) Applicant: Volcano Corporation, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1086 days.

(21) Appl. No.: 14/837,829

(22) Filed: Aug. 27, 2015

(65) Prior Publication Data
US 2016/0058414 A1    Mar. 3, 2016

Related U.S. Application Data

(60) Provisional application No. 62/042,998, filed on Aug. 28, 2014.

(51) Int. Cl.
*A61B 8/00* (2006.01)
*A61B 8/12* (2006.01)
(Continued)

(52) U.S. Cl.
CPC ............ *A61B 8/445* (2013.01); *A61B 5/0066* (2013.01); *A61B 5/0084* (2013.01);
(Continued)

(58) Field of Classification Search
CPC ......... A61B 8/445; A61B 8/4444; A61B 8/14; A61B 8/52; A61B 8/4494; A61B 8/461; A61B 8/12; A61B 8/0891
See application file for complete search history.

(56) References Cited

U.S. PATENT DOCUMENTS 5,313,950 A * 5/1994 Ishikawa ............... A61B 8/12
600/459
5,443,457 A    8/1995 Ginn
(Continued)

FOREIGN PATENT DOCUMENTS

JP         6022961 A     2/1994
JP      2004275200 A     3/2003
(Continued)

*Primary Examiner* — Amelie R Davis
*Assistant Examiner* — Marjan Saboktakin (57) ABSTRACT

Embodiments of the present disclosure are related to intravascular imaging devices having a low reverberation housing and associated systems and methods. In some particular embodiments, the devices of the present disclosure include a transducer housing having a trough on the backside of the ultrasound transducer to deflect ultrasound signals away from the ultrasound transducer. For example, in some implementations an intravascular imaging device is provided that includes a catheter body; a drive cable extending through a lumen of the catheter body; a housing coupled to a distal section of the drive cable; and an ultrasound transducer mounted within the housing, wherein the housing includes a trough on a backside of the ultrasound transducer, the trough shaped to deflect ultrasound signals away from the ultrasound transducer. Methods of making such devices and systems are also provided.

18 Claims, 9 Drawing Sheets

(51) Int. Cl.
*A61B 5/00* (2006.01)
*A61B 8/14* (2006.01)
*A61B 8/08* (2006.01)
*A61M 25/01* (2006.01)

(52) U.S. Cl.
CPC .......... *A61B 5/6851* (2013.01); *A61B 8/0891* (2013.01); *A61B 8/12* (2013.01); *A61B 8/14* (2013.01); *A61B 8/4444* (2013.01); *A61B 8/4494* (2013.01); *A61B 8/461* (2013.01); *A61B 8/52* (2013.01); *A61M 2025/0177* (2013.01)

(56) References Cited

U.S. PATENT DOCUMENTS

| | | | |
|---|---|---|---|
| 2010/0160788 A1* | 6/2010 | Davies | A61B 5/0084 600/467 |
| 2010/0262014 A1* | 10/2010 | Huang | 600/466 |
| 2013/0303920 A1 | 11/2013 | Corl | |
| 2014/0142432 A1 | 5/2014 | Hutchins | |
| 2014/0180076 A1 | 6/2014 | Stigall | |
| 2014/0187959 A1 | 7/2014 | Corl | |

FOREIGN PATENT DOCUMENTS

| | | | | |
|---|---|---|---|---|
| JP | 2004329495 A | 11/2004 | | |
| JP | 2012050706 A | 3/2012 | | |
| WO | 199320880 A1 | 10/1993 | | |
| WO | 199411038 A1 | 5/1994 | | |
| WO | 2005072391 A2 | 8/2005 | | |
| WO | 2013170150 A1 | 11/2013 | | |
| WO | WO-2013170150 A1 * | 11/2013 | ........... | A61B 8/4461 |

\* cited by examiner

Fig. 14

INTRAVASCULAR IMAGING DEVICES HAVING A LOW REVERBERATION HOUSING AND ASSOCIATED SYSTEMS AND METHODS

CROSS REFERENCE TO RELATED APPLICATIONS

The present application claims priority to and the benefit of the U.S. Provisional Patent Application No. 62/042,998, filed Aug. 28, 2014, which is hereby incorporated by reference in its entirety.

TECHNICAL FIELD

The present disclosure relates generally to intravascular devices and, in particular, to imaging catheters having a low reverberation housing for improved imaging fidelity.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. IVUS imaging uses ultrasound echoes to form a cross-sectional image of the vessel of interest. Typically, the ultrasound transducer on an IVUS catheter both emits ultrasound pulses and receives the reflected ultrasound echoes. The ultrasound waves pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound echoes to produce a cross-sectional image of the vessel where the catheter is located.

There are two types of IVUS catheters in common use today: solid-state and rotational, with each having advantages and disadvantages. Solid-state IVUS catheters use an array of ultrasound transducers (typically 64) distributed around the circumference of the catheter and connected to an electronic multiplexer circuit. The multiplexer circuit selects array elements for transmitting an ultrasound pulse and receiving the echo signal. By stepping through a sequence of transmit-receive pairs, the solid-state IVUS system can synthesize the effect of a mechanically scanned transducer element, but without moving parts. Since there is no rotating mechanical element, the transducer array can be placed in direct contact with the blood and vessel tissue with minimal risk of vessel trauma and the solid-state scanner can be wired directly to the imaging system with a simple electrical cable and a standard detachable electrical connector.

In the typical rotational IVUS catheter, a single ultrasound transducer element fabricated from a piezoelectric ceramic material is located at the tip of a flexible driveshaft that spins inside a plastic sheath inserted into the vessel of interest. The transducer element is oriented such that the ultrasound beam propagates generally perpendicular to the axis of the catheter. The fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of several hundred of these ultrasound pulse/echo acquisition sequences occurring during a single revolution of the transducer.

While the solid-state IVUS catheter is simple to use due to its lack of moving parts, it cannot match the image quality available from a rotational IVUS catheter. It is difficult to operate a solid-state IVUS catheter at the same high frequency as a rotational IVUS device, and the lower operating frequency of solid-state IVUS catheters translates into poorer resolution compared to that of a higher frequency rotational IVUS catheter. There are also artifacts such as sidelobes, grating lobes, and poor elevation focus (perpendicular to the imaging plane) that arise from the array-based imaging that are greatly reduced or completely absent with a rotational IVUS device. Despite the image quality advantages of the rotational IVUS catheter, each of these devices has found a niche in the interventional cardiology market, with solid-state IVUS preferred in circumstances where ease-of-use is paramount and the reduced image quality is acceptable for the particular diagnostic needs, while rotational IVUS is preferred where image quality is paramount and the more time-consuming catheter preparation is justified.

In the rotational IVUS catheter, the ultrasound transducer is typically a piezoelectric ceramic element with low electrical impedance capable of directly driving an electrical cable connecting the transducer to the imaging system hardware. In this case, a single pair of electrical leads (or coaxial cable) is used to carry the transmit pulse from the system to the transducer and to carry the received echo signals from the transducer back to the imaging system by way of a patient interface module, where they are assembled into an image. For further improvement in image quality in rotational IVUS imaging, it is desirable to use a transducer with broader bandwidth and to incorporate focusing into the transducer. The piezoelectric micro-machined ultrasound transducer (PMUT) fabricated using a polymer piezoelectric material, such as disclosed in U.S. Pat. No. 6,641,540, offers greater than 100% bandwidth for optimum resolution in the radial direction, and a spherically-focused aperture for optimum azimuthal and elevation resolution.

Current transducer housings used in IVUS catheter designs include a large hole or opening in back of the ultrasound transducer. This hole is filled with backing material when the transducer assembly is mounted into the housing. The intended purpose of that backing-filled hole is to dissipate any sound waves that emerge from the back of the transducer. Unfortunately, the small size of the transducer housing leaves only about 300 μm of space for the backing material, and depending on the backing material used, that may not be enough to adequately dampen the sound waves that enter the backing. In fact, in some current designs, there is only about 30 dB of round trip attenuation for the sound waves propagating through the backing and reflecting from the rear surface of the backing material. Furthermore, the large opening in the housing—that must be at least as large as the transducer aperture—leaves very little structural material to maintain the integrity of the housing since the housing necessarily includes a significant opening on the front side of the transducer to allow the ultrasound signals to be sent and received. As a result, there are only two very thin struts of structure remaining to connect the proximal part of the housing, which is typically welded to the flexible drive cable, to the distal portion of the housing defining the bullet nose tip.

Accordingly, there remains a need for intravascular imaging devices, systems, and methods that include an improved imaging transducer housing having improved sound dampening properties and/or structural integrity.

SUMMARY

Embodiments of the present disclosure are directed to intravascular imaging devices having a low-reverberation housing that is also structurally stronger than traditional designs.

In some instances, an intravascular imaging device is provided that includes: a catheter body; a drive cable extending through a lumen of the catheter body; a housing coupled to a distal section of the drive cable; and an ultrasound transducer mounted within the housing, wherein the housing includes a trough on a backside of the ultrasound transducer, the trough shaped to deflect ultrasound signals away from the ultrasound transducer. The trough can have an arcuate profile along a longitudinal axis of the housing. In that regard, the arcuate profile of the trough can have a constant or variable radius of curvature along the longitudinal axis of the housing. The trough can also have an arcuate profile, constant or variable, in a plane extending perpendicular to the longitudinal axis of the housing. The trough can be shaped to deflect ultrasound signals along a longitudinal axis of the housing, either proximally or distally. The trough can be filled with a backing material.

Associated systems and methods are also provided. For example, an intravascular imaging system can include: an intravascular imaging device, including: a catheter body; a drive cable extending through a lumen of the catheter body; a housing coupled to a distal section of the drive cable; and an ultrasound transducer mounted within the housing, wherein the housing includes a trough on a backside of the ultrasound transducer, the trough shaped to deflect ultrasound signals away from the ultrasound transducer; and a processing system in communication with the intravascular imaging device, the processing system configured to process data obtained by the intravascular imaging device. The system can also include a patient interface module configured to interface with a proximal portion of the intravascular imaging device and communicate with the processing system. Further, a display in communication with the processing system can be utilized to visualize information obtained by the intravascular imaging device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
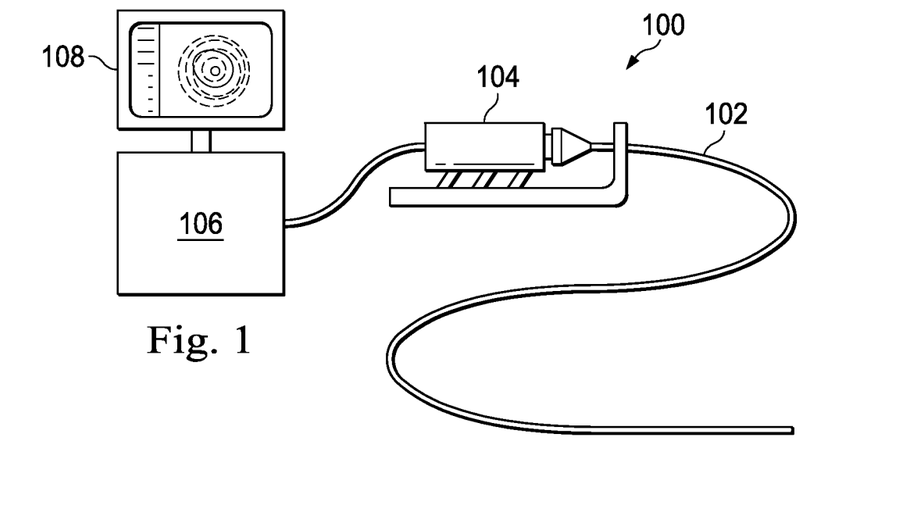
FIG. 1 is a diagrammatic schematic view of an imaging system according to an embodiment of the present disclosure.

Referring to FIG. 1, shown therein is an IVUS imaging system 100 according to an embodiment of the present disclosure. In some embodiments of the present disclosure, the IVUS imaging system 100 is a lead-zirconate-titanate (PZT) or piezoelectric micro-machined ultrasound transducer (PMUT) rotational IVUS imaging system. For brevity, the following description will utilize a PMUT rotational IVUS imaging system for illustrative purposes only. In that regard, the main components of the PMUT rotational IVUS imaging system are the PMUT rotational IVUS catheter 102, a PMUT catheter compatible patient interface module (PIM)

104, an IVUS console or processing system 106, and a monitor 108 to display the IVUS images generated by the IVUS console 106.

Figure 2:
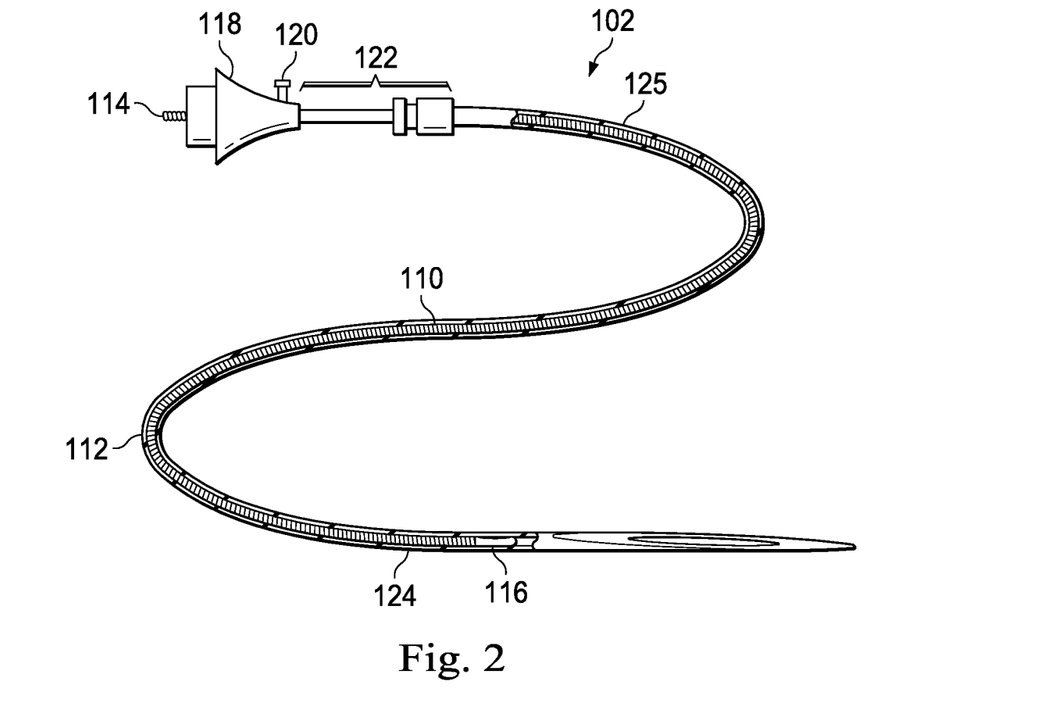
FIG. 2 is a diagrammatic, partial cutaway perspective view of an imaging device according to an embodiment of the present disclosure.

Referring now to FIG. 2, shown therein is a diagrammatic, partial cutaway perspective view of the PMUT catheter 102 according to an embodiment of the present disclosure. In that regard, FIG. 2 shows additional detail regarding the construction of the PMUT rotational IVUS catheter 102. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the PMUT rotational IVUS catheter 102 includes an imaging core 110 and an outer catheter/sheath assembly 112. The imaging core 110 includes a flexible drive shaft that is terminated at the proximal end by a rotational interface 114 providing electrical and mechanical coupling to the PIM 104 of FIG. 1. The distal end of the flexible drive shaft of the imaging core 110 is coupled to a transducer housing 116 containing the PMUT and associated circuitry. The catheter/sheath assembly 112 includes a hub 118 that supports the rotational interface and provides a bearing surface and a fluid seal between the rotating and non-rotating elements of the catheter assembly. The hub 118 includes a Luer lock flush port 120 through which saline is injected to flush out the air and fill the inner lumen of the sheath with an ultrasound-compatible fluid at the time of use of the catheter. The saline or other similar flush is typically required since ultrasound does not readily propagate through air. Saline also provides a biocompatible lubricant for the rotating driveshaft. The hub 118 is coupled to a telescope 122 that includes nested tubular elements and a sliding fluid seal that permit the catheter/sheath assembly 112 to be lengthened or shortened to facilitate axial movement of the transducer housing within an acoustically transparent window 124 of the distal portion of the catheter 102. In some embodiments, the window 124 is composed of thin-walled plastic tubing fabricated from material(s) that readily conduct ultrasound waves between the transducer and the vessel tissue with minimal attenuation, reflection, or refraction. A proximal shaft 125 of the catheter/sheath assembly 112 bridges the segment between the telescope 122 and the window 124, and is composed of a material or composite that provides a lubricious internal lumen and optimum stiffness, but without the need to conduct ultrasound.

Figure 3:
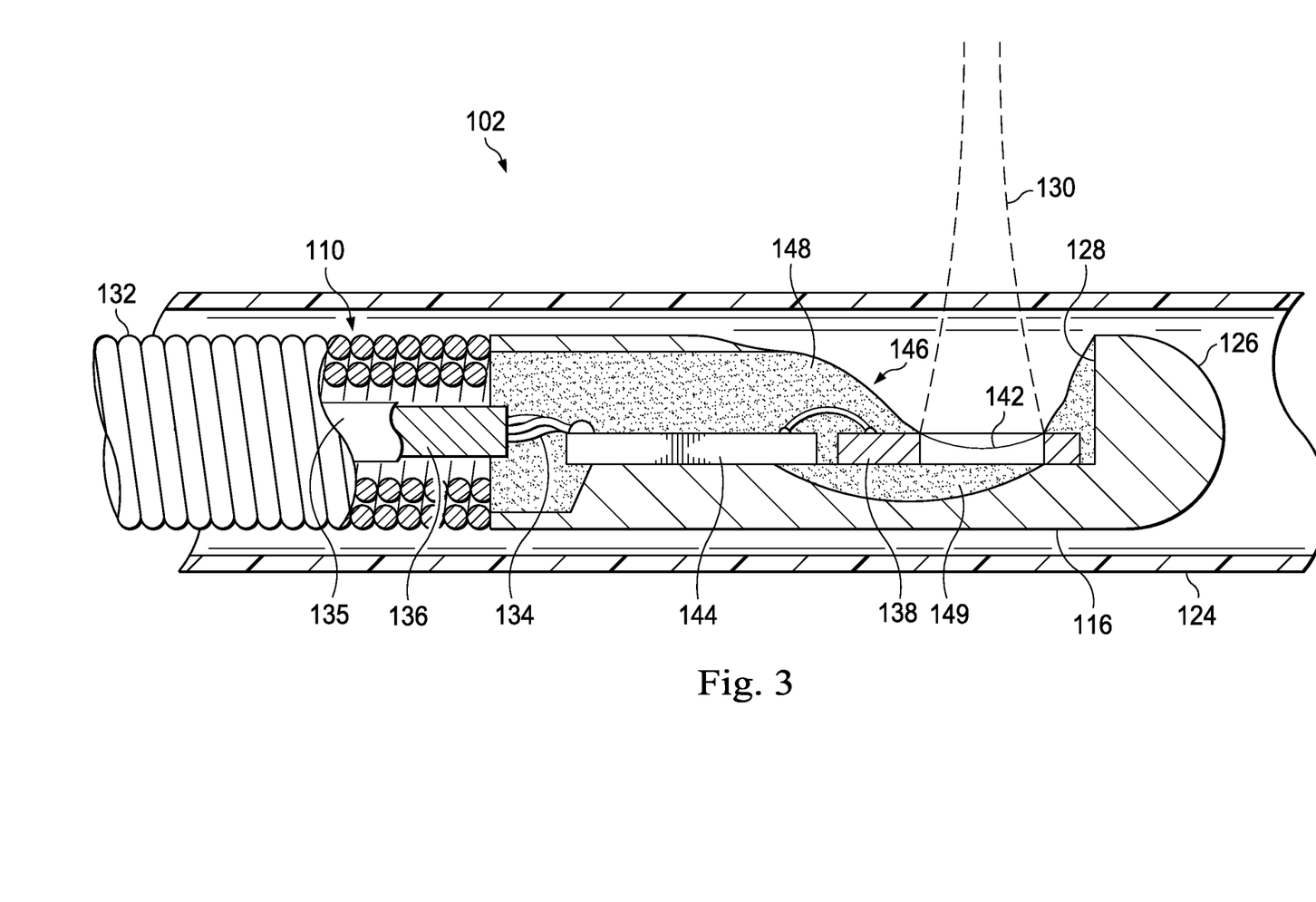
FIG. 3 is a diagrammatic, cross-sectional side view of a distal portion of an imaging device according to an embodiment of the present disclosure.

Referring now to FIG. 3, shown therein is a cross-sectional side view of a distal portion of the catheter 102 according to an embodiment of the present disclosure. In particular, FIG. 3 shows an expanded view of aspects of the distal portion of the imaging core 110. In this exemplary embodiment, the imaging core 110 is terminated at its distal tip by a housing 116 fabricated from stainless steel and provided with a rounded nose 126 and a cutout 128 for the ultrasound beam 130 to emerge from the housing 116. In some embodiments, the flexible driveshaft 132 of the imaging core 110 is composed of two or more layers of counter wound stainless steel wires, welded, or otherwise secured to the housing 116 such that rotation of the flexible driveshaft also imparts rotation on the housing 116. In the illustrated embodiment, the ASIC 144 and the MEMS 138 components are wire-bonded and glued together to form an ASIC/MEMS hybrid assembly 146, which is mounted to the transducer housing 116 and secured in place with epoxy 148. The leads of the multi-conductor electrical cable 134 with optional shield 136 and jacket 135 are soldered or otherwise electrically coupled directly to the ASIC 144 in this embodiment. The electrical cable 134 extends through an inner lumen of the flexible driveshaft 132 to the proximal end of the imaging core 110 where it is terminated to the electrical connector portion of the rotational interface 114 shown in FIG. 2.

When assembled together, as shown in FIG. 3, the PMUT MEMS 138 and the ASIC 144 form an ASIC/MEMS hybrid assembly 146 that is mounted within the housing 116, with the ASIC 144 electrically coupled to the PMUT MEMS 138 through two or more connections such as wire bonds. In that regard, in some embodiments of the present disclosure the ASIC 144 includes an amplifier, a transmitter, and a protection circuit associated with the PMUT MEMS as discussed above. The PMUT MEMS 138 includes a spherically focused ultrasound transducer 142. In the illustrated embodiment, the connections between the ASIC 144 and MEMS 138 are provided by wire bonds, while in other embodiments, the ASIC 144 is flip-chip mounted to the substrate of the PMUT MEMS 138 using anisotropic conductive adhesive or suitable alternative chip-to-chip bonding method. In still other embodiments, both ASIC 144 and MEMS 138 components are attached to a flexible circuit substrate which includes conductive paths to electrically connect the two components.

Further in reference to FIG. 3, the ASIC/MEMS hybrid assembly 146 is secured in place relative to the housing 116 by an epoxy 148 or other bonding agent. As discussed in greater detail below, the epoxy 148 also serves as an encapsulant for the ASIC/MEMS hybrid assembly 146, as insulation and strain relief for the wire bonds, and as insulation and strain relief for the electrical cable 134 where it is soldered to the ASIC/MEMS hybrid assembly 146. Additional epoxy 149 of the same or different composition fills the recess behind the ultrasound transducer 142, serving as an acoustic backing material to absorb acoustic waves propagating in or out of the back side of the transducer 142.

Figure 4:
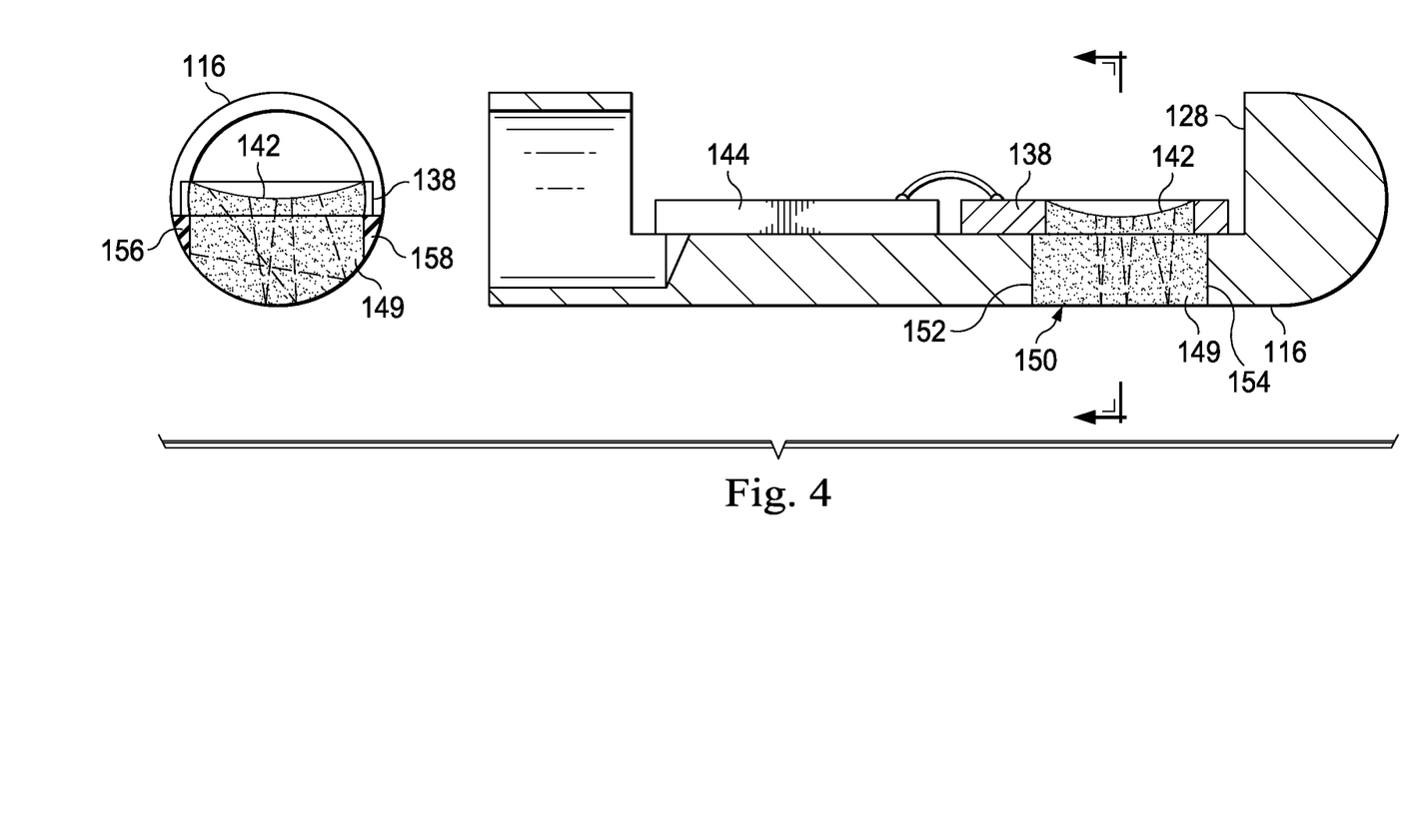
FIG. 4 provides diagrammatic cross-sectional side and end views of a transducer housing.

FIG. 4 provides diagrammatic cross-sectional side and end views of a transducer housing 116. As shown, backing material 149 fills an opening or hole 150 in the transducer housing 116 formed adjacent the backside of the PMUT MEMS 138. Typically, the same type of backing material fills a well formed in the back side of the PMUT MEMS 138. As shown, the opening 150 extends through the housing 116 in a direction perpendicular to the longitudinal axis of the housing 116. As a result, sidewalls 152, 154, 156, and 158 defining the opening 150 each extend perpendicular to the longitudinal axis of the housing 116. FIG. 4 also illustrates exemplary paths for ultrasound signals propagating out the back side of the PMUT and reflecting off of the bottom surface of the backing material 149. As shown, sound waves coming from anywhere along a strip down the middle of the transducer will return directly to the transducer after a single bounce off the bottom surface of the backing material 149. Note also that, as a result of the opening 150 being opposite the cutout 128, the distal and proximal portions of the housing 116 are only connected by two small struts, each having an approximately triangular cross-section, and whose inner surfaces define sidewalls 156 and 158, as best seen in the cross-sectional end view on the left side of FIG. 4.

Embodiments of the present disclosure replace the opening 150 formed behind the transducer of the PMUT MEMS 138 with a trough. In that regard, the trough is sized and shaped to deflect any sound waves emerging from the back side of the transducer in a manner such that they are forced to follow a long pathway with multiple reflections before returning to the transducer. Accordingly, in some instances the trough is sized and shaped such that the first reflection of the ultrasound signals propagate generally along the length of the housing 116 rather than through its radius. This long pathway, with the multiple reflections produces greater attenuation compared to a single short round-trip path illustrated in FIG. 4. In addition, the chaotic pathways for the different portions of the ultrasound beam emerging from the back of the transducer create incoherence for the reverberations, further diminishing any acoustic artifact due to the backing configuration. The trough can incorporate various shapes, textures, or features to enhance the acoustic losses. For example, the housing can be fabricated by machining, grinding, electrical discharge machining (EDM), and/or molding, and each of these different fabrication techniques places different constraints on the feasible trough shapes and other features. Some simple exemplary trough structures are illustrated and described below that could be fabricated using a milling or grinding method, while EDM or molding could implement more intricate features.

Further, a trough design leaves much more of the housing material intact, and in a more favorable configuration, greatly increasing the axial, flexural, and torsional stiffness of the structure. As a result, the structural integrity of the housing 116 and the imaging core as a whole is improved. Further still, the strengthened, low reverberation transducer housings of the present disclosure can also incorporate other desirable features, such as alignment features to ensure proper placement of the hybrid transducer assembly 146 within the housing 116. In fact, such alignment features are particularly useful in the context of a hybrid transducer structure that maintains a precise positional relationship between the ASIC and MEMS components. In that regard, the present disclosure also provides a manufacturing method to facilitate such precise positioning.

Figure 5:
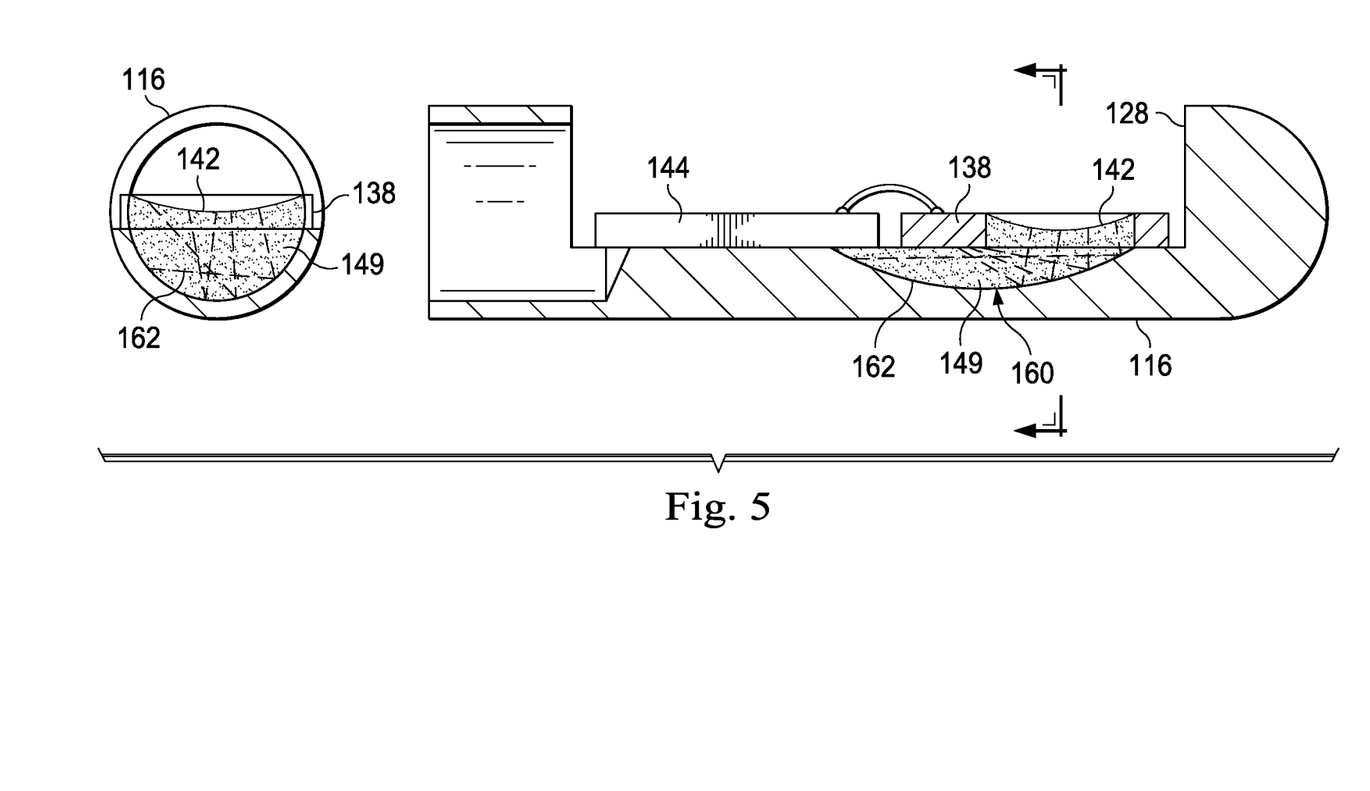
FIG. 5 provides diagrammatic cross-sectional side and end views of a transducer housing according to an embodiment of the present disclosure.

FIG. 5 provides diagrammatic cross-sectional side and end views of a transducer housing according to an embodiment of the present disclosure. As shown, instead of the opening 150, the transducer housing 116 includes a trough 160 formed adjacent the backside of the PMUT MEMS 138. The trough 160 is defined as a recess in the material of the housing 116. In particular, the trough 160 is defined by an arcuate surface 162 that extends along the longitudinal axis of the housing 116 (as shown in the side view on the right side of FIG. 5) and transverse to the longitudinal axis of the housing 116 (as shown in the end view on the left side of FIG. 5). In the illustrated embodiment, the arcuate surface 162 has a substantially constant radius of curvature in both the longitudinal and transverse directions. In other embodiments, the arcuate surface 162 has a variable radius of curvature in at least one of the longitudinal and transverse directions. FIG. 5 also illustrates exemplary paths for ultrasound signals propagating out the back side of the PMUT and bouncing off the surface 162 defining the trough. As shown, the sound waves travel diverse paths from the back of the transducer, generally propagating along the longitudinal axis of the housing within the backing material 149, and following a long path before returning to the transducer 142. The signal strength is diminished by the long propagation distance and by the multiple reflections. Reflections at oblique angles, in particular, cause increased loss due to mode conversion into shear waves (and other modes) that are even more rapidly attenuated than the longitudinal waves of interest for IVUS. In addition, the diversity of path lengths causes any reverberations returning to the transducer to add together incoherently. Note also that, as a result of having the trough 160 instead of the opening 150, the distal and proximal portions of the housing 116 are connected by an approximately half-cylindrical shell of the housing material along the entire length of the housing. Thus, the structural integrity of the housing 116 is substantially increased.

Figure 6:
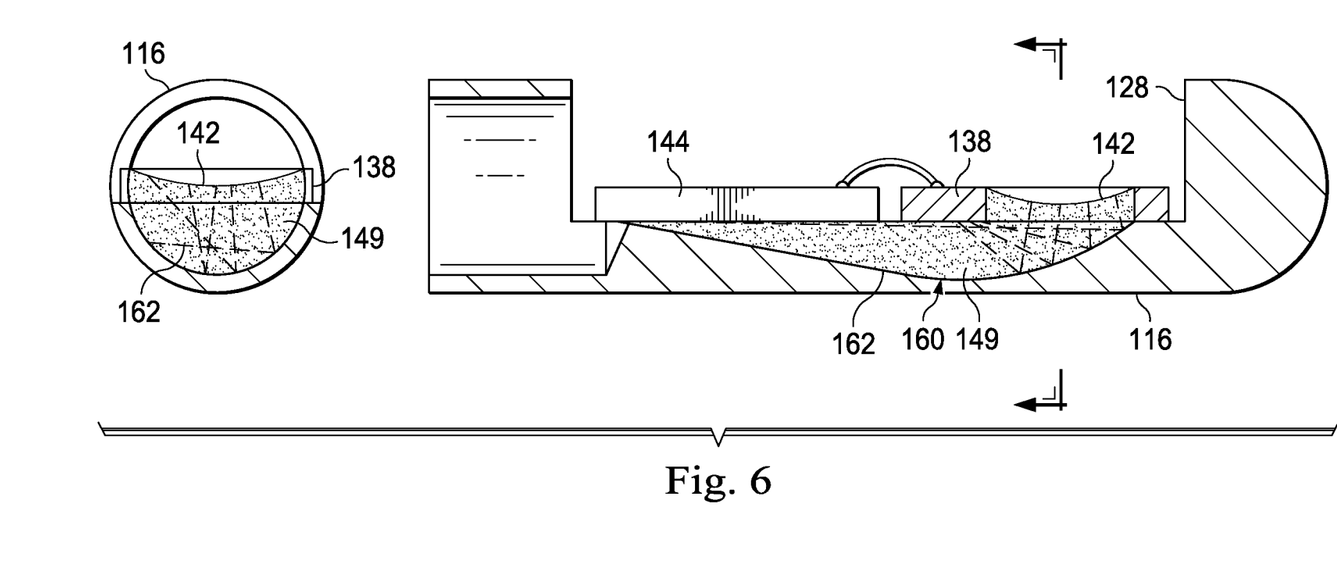
FIG. 6 is a diagrammatic cross-sectional side view of a transducer housing according to an embodiment of the present disclosure.

It is understood that numerous variations to the trough 160 are made in other implementations. For example, the trough can be elongated (or shortened) to extend along a greater (or shorter) length of the housing. In that regard, the trough 160 can be extended proximally such that it merges with the axial hole through the proximal end of the housing that receives the drive cable, thereby providing an even longer axial pathway for dissipation of the reverberations. As a result, the length of trough 160 and corresponding length available for absorption of the sound waves can extend up to several millimeters in length in a single direction, instead of approximately 300 micrometers in the design of FIG. 4. FIG. 6 illustrates an exemplary embodiment of a housing 116 having an elongated trough 170. In that regard, the depth of the elongated trough 170 gradually tapers as it extends proximally from the transducer 142. The trough 170 can have a constant or variable taper.

The surface 162 of the trough 160 can also include texture or bumps, designed to further scatter the ultrasound. As a result of the increased attenuation and scattering of ultrasound propagating within the trough-shaped backing material, a larger range of backing materials can be considered, including lower loss materials (e.g., unfilled epoxy or other curable polymer material), which may otherwise provide favorable acoustic properties, such as low acoustic impedance.

Figure 7:
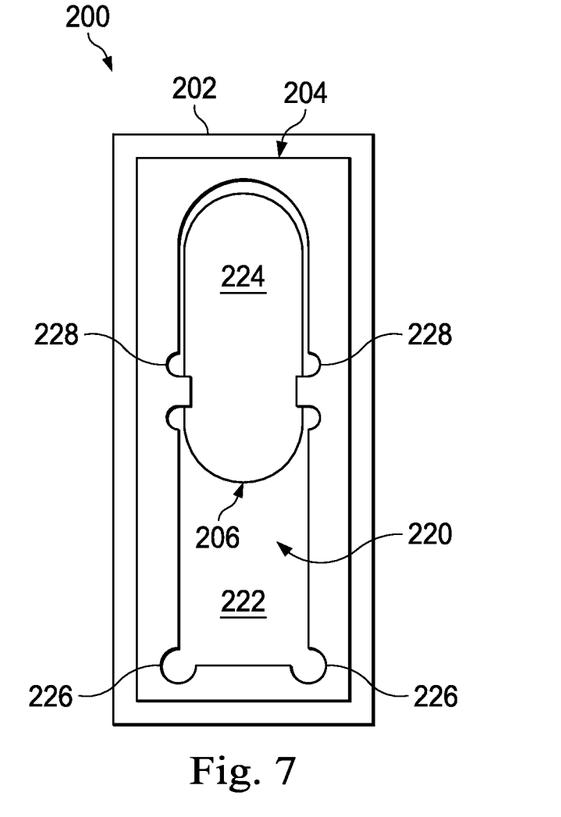
FIG. 7 is a diagrammatic top view of an assembly template according to an embodiment of the present disclosure.
Figure 8:
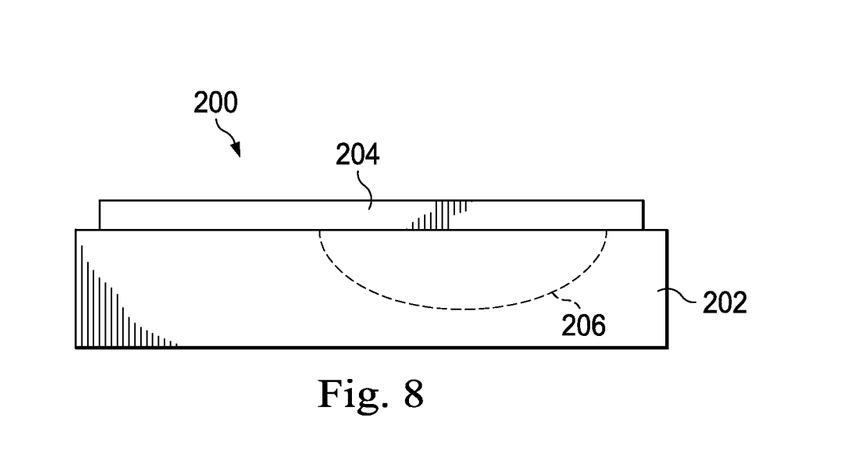
FIG. 8 is a diagrammatic side view of an assembly template according to an embodiment of the present disclosure.
Figure 9:
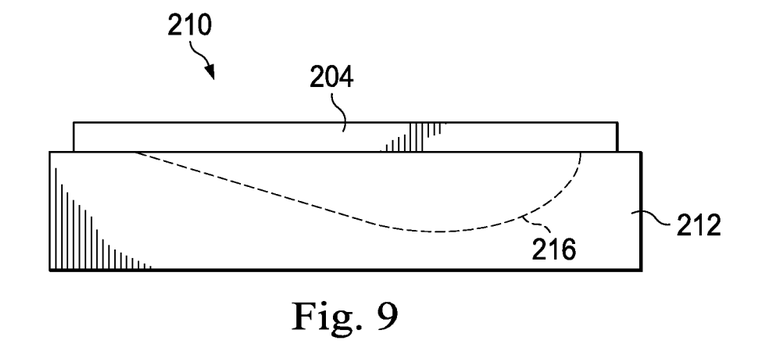
FIG. 9 is a diagrammatic side view of an assembly template according to another embodiment of the present disclosure.

Referring generally to FIGS. 7-14, various aspects of methods of assembling an intravascular imaging device and, in particular, a hybrid transducer assembly that includes an ASIC and PMUT MEMS will be described. Referring initially to FIGS. 7 and 8, shown therein is an alignment template 200 that includes a base component 202 and a top component 204. As shown in FIG. 8, the base component 202 includes a trough 206. As will be described below, in some implementations, the trough 206 is sized and shaped to mate with a corresponding trough in a transducer housing (such as trough 160 shown in FIG. 5). As a result, the size and shape of the trough in the base component 202 can vary accordingly with the features of the transducer housing in which the hybrid transducer assembly is to be used. For example, FIG. 9 illustrates an alignment template 210 that includes a base component 212 having a trough 216 that is configured to match the trough 170 of the housing shown in FIG. 6. Generally speaking, the base component 202 and the top component 204 of the alignment template 200 can be formed of any suitable metal or plastic that can withstand the processing steps described below, which can include wire bonding, gluing, epoxy bonding, molding, etc.

Referring again to FIG. 7, the top component 204 of the alignment template 200 includes a recess 220 that defines recessed areas 222 and 224 for receiving the ASIC 144 and PMUT MEMS 138, respectively. In that regard, the recess 220 in the metal or plastic substrate defining top component 204 is typically less than the die thickness of the PMUT MEMS 138. For example, in some instances the PMUT MEMS 138 has a 75 µm die thickness, and the recess 220 has a depth of ~50 µm (2 mils). The recess 220 also includes various structural features, such as regions 226 and 228, that facilitate precise alignment of the ASIC 144 and the PMUT MEMS 138 relative to one another and/or allow grasping of the ASIC 144 and the PMUT MEMS 138 by a tool for insertion/removal from the alignment template 200. In some instances, an inner surface of the housing 116 includes similar structural features to facilitate proper placement of the hybrid transducer assembly within the housing and relative to the trough.

Figure 10:
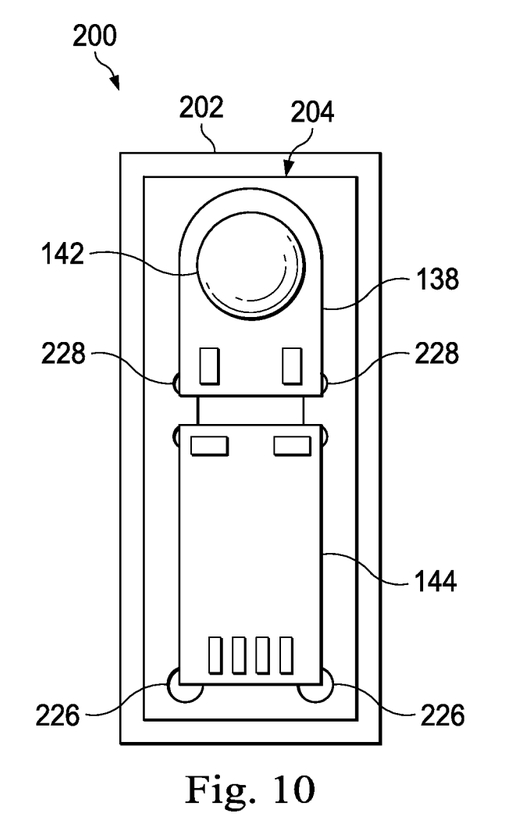
FIG. 10 is a diagrammatic top view of an assembly template having an application-specific integrated circuit (ASIC) and microelectromechanical system (MEMS) component mounted therein according to an embodiment of the present disclosure.
Figure 11:
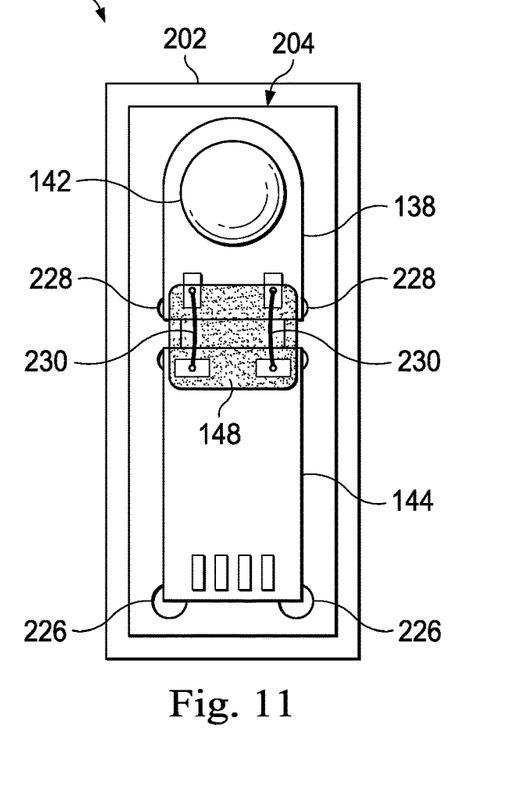
FIG. 11 is a diagrammatic top view of the assembly template of FIG. 10 showing the ASIC and MEMS component coupled to one another according to an embodiment of the present disclosure.
Figure 12:
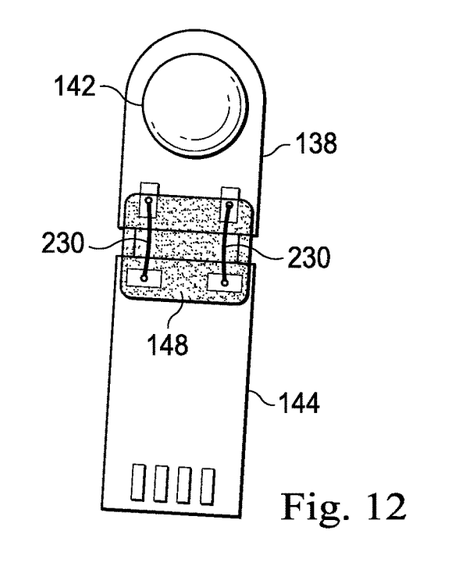
FIG. 12 is a diagrammatic top view of the ASIC and MEMS component coupled to one another and removed from the assembly template of FIGS. 10 and 11 according to an embodiment of the present disclosure.

Referring now to FIG. 10, the ASIC 144 and the PMUT MEMS 138 are shown positioned within the alignment template 200 that holds the ASIC 144 and the PMUT MEMS 138 in their desired relative positions prior to wire bonding. FIG. 11 shows the ASIC 144 and the PMUT MEMS 138 electrically coupled to one another via wire bonds 230 while held in the alignment template 200. The wire bonds 230 are subsequently potted with epoxy 148, as shown, to provide insulation and strain relief. The epoxy 148 also provides a mechanical connection between the ASIC 144 and the PMUT MEMS 138 to hold the alignment between the components. FIG. 12 shows that electrically and physically coupled ASIC 144 and PMUT MEMS 138 hybrid assembly 146 removed from the alignment template 200.

Figure 13:
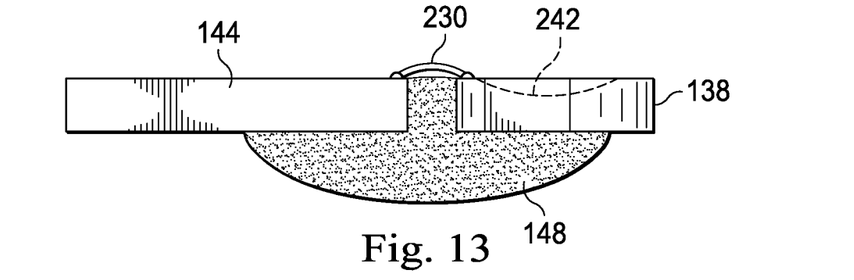
FIG. 13 is a diagrammatic side view of the ASIC and MEMS component coupled to one another according to an embodiment of the present disclosure.
Figure 14:
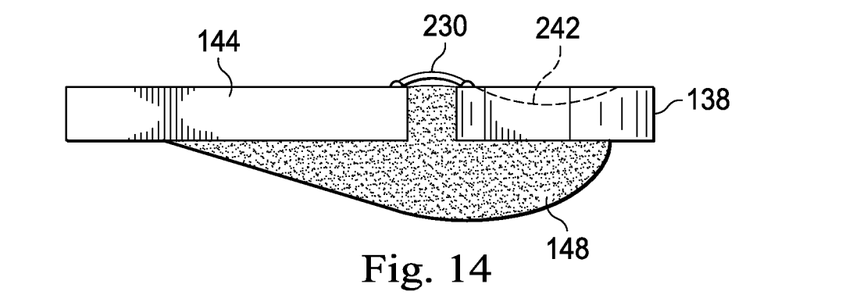
FIG. 14 is a diagrammatic side view of the ASIC and MEMS component coupled to one another according to another embodiment of the present disclosure.

It should be noted that the top component 204 of the alignment template 200 can be utilized to electrically and physically couple the ASIC 144 and the PMUT MEMS 138 in this manner without use of the trough-containing base component 202. However in some embodiments, the trough 206/216 of the base component 202/212 can be utilized as a mold to form the desired backing configuration behind the PMUT MEMS 138 and ASIC 144, as a part of the ASIC/MEMS hybrid assembly 146. In that regard, the backing material 149 can be introduced prior to placing the ASIC 144 and/or PMUT MEMS 138 in the alignment template, after placing the ASIC 144 and/or PMUT MEMS 138 in the alignment template but prior to the wire bonding step, or after the wire bonding is completed. The backing material may be the same composition as that used for adhesive strain relief of the bond wires 230, in which case it may be applied simultaneously with the encapsulation of the bond wires 230. FIGS. 13 and 14 illustrate representative embodiments of such hybrid transducer assemblies where the trough 206/216 of the base component 202/212 has been utilized to form a desired backing material configuration. The resulting "hull" of backing material 149 in FIGS. 13 and 14 provides a stronger mechanical support for the hybrid transducer assembly than the small section of epoxy used for strain-relieving the wires. In such embodiments, the housing 116 can include a slightly oversized trough, sized and shaped to accommodate the hull that is now part of the hybrid transducer assembly.

With respect to the oversized housing trough, if the housing trough is sized and shaped to provide sufficient clearance, it can accommodate a hybrid transducer assembly (including the hull of backing material) that is conformally coated with a thin film of Parylene. Such a conformal Parylene coating is desirable to provide reliable electrical insulation and moisture protection for the ASIC/MEMS hybrid assembly 146 and cable 134 attachment. Without sufficient clearance within the housing trough, the hull would need to be masked during the coating process, compromising the integrity of the Parylene film. Accordingly, this approach of accommodating the conformal Parylene coating within an oversized housing trough simplifies the assembly process by eliminating the Parylene masking/trimming steps, and it improves the Parylene integrity by maintaining the continuity of the film over the entire hybrid assembly. As a result, simpler manufacturing is provided in combination with increased performance and reliability. Furthermore, without the shaped hull as described above, simply applying a Parylene conformal coating to the back of the PMUT MEMS 138 would introduce a potentially problematic interface close to, and generally parallel to, the transducer surface. Such an interface, close to the transducer would introduce reverberations within the backing that could degrade the performance of the transducer. In contrast, the hull of backing material moves the Parylene interface further away from transducer and it shapes the interface so as to deflect any acoustic waves emerging from the back of the transducer 142 generally along the axial aspect of the trough where they will be attenuated before they can return to the back side of the transducer 142.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular imaging device, comprising:
   a catheter body;
   a drive cable extending through a lumen of the catheter body;
   a housing coupled to a distal section of the drive cable; and
   an ultrasound transducer mounted within the housing parallel to a longitudinal axis of the housing such that the ultrasound transducer is configured to transmit, from a front side of the ultrasound transducer, a first portion of ultrasound signals perpendicular to the longitudinal axis,
   wherein a backside of the ultrasound transducer is arranged over a trough formed in the housing,
   wherein the trough includes an arcuate profile along the longitudinal axis, wherein the arcuate profile includes a surface oblique to the longitudinal axis and shaped to deflect a second portion of the ultrasound signals from the backside away from the ultrasound transducer proximally along the longitudinal axis.

2. The device of claim 1, wherein the arcuate profile of the trough has a constant radius of curvature along the longitudinal axis of the housing.

3. The device of claim 1, wherein the arcuate profile of the trough has a variable radius of curvature along the longitudinal axis of the housing.

4. The device of claim 1, wherein the trough has an arcuate profile in a plane extending perpendicular to the longitudinal axis of the housing such that the trough has an arcuate profile in two different planes perpendicular to one another.

5. The device of claim 4, wherein the arcuate profile of the trough in the plane extending perpendicular to the longitudinal axis of the housing has a constant radius of curvature.

6. The device of claim 1, wherein a space between the ultrasound transducer and the trough is filled with a backing material, wherein the surface oblique to the longitudinal axis is shaped to deflect the second portion of the ultrasound signals from the backside away from the ultrasound transducer proximally along the longitudinal axis and within the backing material.

7. The device of claim 1, further comprising an application-specific integrated circuit (ASIC) mounted within the housing and electrically coupled to the ultrasound transducer.

8. The device of claim 1, wherein the ultrasound transducer is selected from the group consisting of a piezoelectric ultrasound transducer and a micro-machined transducer.

9. The device of claim 7, wherein the ASIC is further mechanically coupled to the ultrasound transducer.

10. The device of claim 7, wherein the ultrasound transducer and ASIC are coated for insulation.

11. The device of claim 1, wherein the housing comprises a rounded end, wherein the trough is spaced from the rounded end of the housing.

12. The device of claim 11, wherein the ultrasound transducer is mounted within the housing such that the second portion of the ultrasound signals is directed to the trough and not the rounded end of the housing.

13. The device of claim 1, wherein the trough is shaped to receive a molded acoustic backing.

14. An intravascular imaging system, comprising:
an intravascular imaging device, including:
a catheter body;
a drive cable extending through a lumen of the catheter body;
a housing coupled to a distal section of the drive cable; and
an ultrasound transducer mounted within the housing parallel to a longitudinal axis of the housing such that the ultrasound transducer is configured to transmit, from a front side of the ultrasound transducer, a first portion of ultrasound signals perpendicular to the longitudinal axis,
wherein a backside of the ultrasound transducer is arranged over a trough formed in the housing,
wherein the trough includes an arcuate profile along the longitudinal axis, wherein the arcuate profile includes a surface oblique to the longitudinal axis and shaped to deflect a second portion of the ultrasound signals from the backside away from the ultrasound transducer proximally along the longitudinal axis; and
a processing system in communication with the intravascular imaging device, the processing system configured to process data obtained by the intravascular imaging device.

15. The system of claim 14, further comprising a patient interface module configured to interface with a proximal portion of the intravascular imaging device and communicate with the processing system.

16. The system of claim 14, further comprising a display in communication with the processing system.

17. The system of claim 14, wherein the ultrasound transducer is selected from the group consisting of a piezoelectric ultrasound transducer and a micro-machined transducer.

18. The system of claim 14, wherein the device further comprises an application-specific integrated circuit (ASIC) mounted within the housing and electrically coupled to the ultrasound transducer.

* * * * *